United States Patent [19]

Aihara

[11] Patent Number: 4,608,980

[45] Date of Patent: Sep. 2, 1986

[54] LASER HAND PIECE

[75] Inventor: Takao Aihara, Tokyo, Japan

[73] Assignee: Osada Electric Co., Ltd., Tokyo, Japan

[21] Appl. No.: 599,762

[22] Filed: Apr. 13, 1984

[51] Int. Cl.⁴ ............................................. A61B 17/36
[52] U.S. Cl. ................................................. 128/303.1
[58] Field of Search ............ 128/4, 6, 303.1, 395–398; 350/422, 257

[56] References Cited

U.S. PATENT DOCUMENTS

| | | | |
|---|---|---|---|
| 4,076,018 | 2/1978 | Heckele | 128/6 |
| 4,141,362 | 2/1979 | Wurster | 128/395 |
| 4,146,019 | 3/1979 | Bass et al. | 128/6 |
| 4,451,131 | 5/1984 | Shimizu | 350/257 |
| 4,503,853 | 3/1985 | Ota et al. | 128/303.1 |
| 4,517,962 | 5/1985 | Heckele | 128/6 |

FOREIGN PATENT DOCUMENTS 3143421 5/1982 Fed. Rep. of Germany ... 128/303.1

Primary Examiner—Edward M. Coven
Assistant Examiner—Max F. Hindenberg
Attorney, Agent, or Firm—Burgess, Ryan & Wayne

[57] ABSTRACT

A laser hand piece comprises a shank on which is attached the light emitting end of a laser transmission means, a head having a laser light reflecting means and a laser light converging means and a head attachment means for releasably attaching the head to the leading end of the shank. A suitable head is selected from the group comprising heads having an optical means of a different focal length, heads provided with optical means for emitting the laser light in different directions and heads provided with a water supply means and/or air supply means. Therefore, depending upon an affected or diseased part of a body to be treated or operated, a suitable head can be selected and releasably attached to the shank by an operator.

7 Claims, 16 Drawing Figures

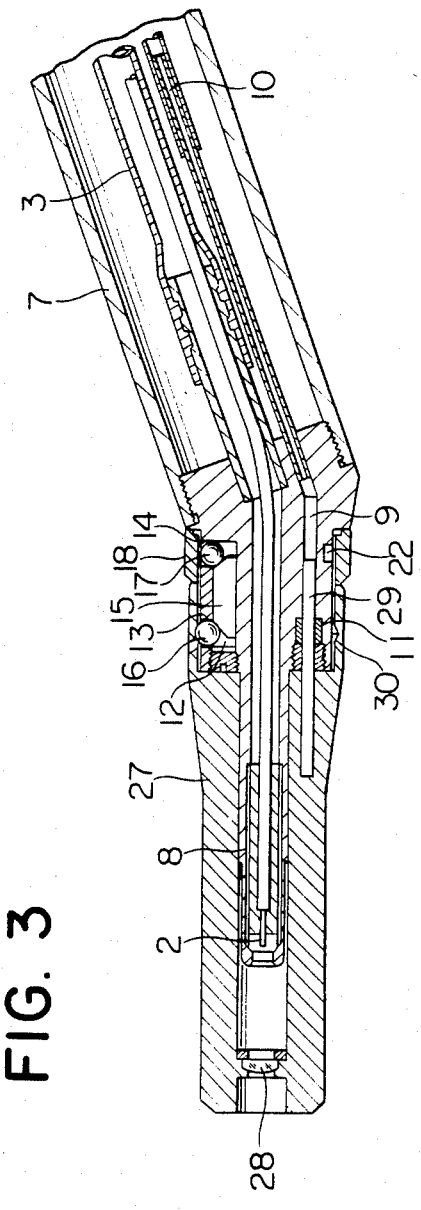
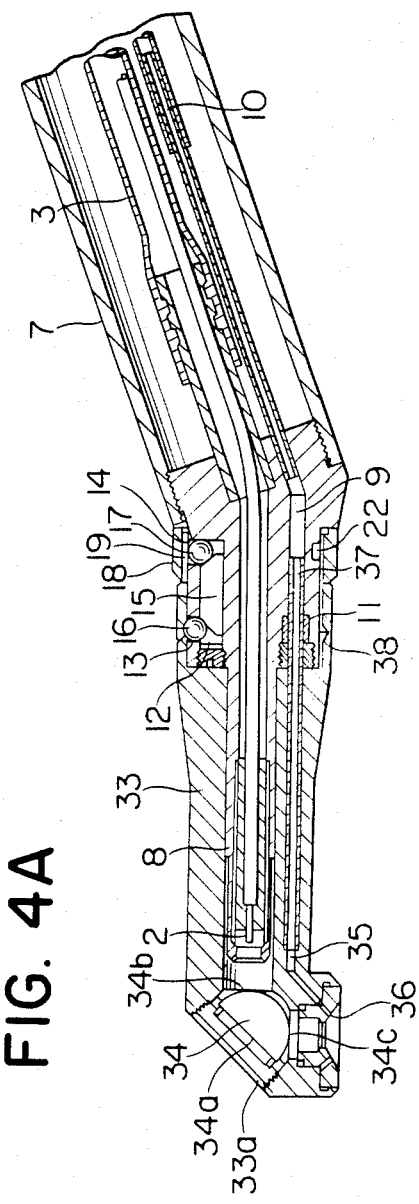
FIG. 3
FIG. 4A

LASER HAND PIECE

BACKGROUND OF THE INVENTION

So far depending upon an affected or diseased part of a body, a laser hand piece of a suitable focal length which emits the laser light in a predetermined direction must be selected. The prior art laser hand pieces comprise, in general, a shank into which is housed a laser light converging means or into which are housed a laser light converging means and a laser light reflecting means. The shank is securely attached to the leading end of a laser light transmission means and a plug which interconnects between the laser light transmission means and a laser light oscillator is securely attached to the rear end of the laser light transmission means. As a result, in order to change the function of a laser hand piece, the laser light transmission means as well as the plug which are associated with the shank must be also replaced. As a consequence, it is very cumbersome to change the function of a laser hand piece. Furthermore, each shank is provided with a laser light transmission means and a plug, so that the cost of the laser hand piece is expensive and the cost for repair and maintenance of the laser hand piece is also expensive. In addition, when a laser hand piece is used in the cases of surgical operations, there arises the problem that the laser hand piece must be sterilized or disinfected in a complicated manner.

SUMMARY OF THE INVENTION

One of the objects of the present invention is therefore to provide a laser hand piece in which a suitable head can be replaced by an operator depending upon an affected or diseased part of a body.

Another object of the present invention is to provide a laser hand piece in which a suitable head can be selected from the group consisting of heads of different focal length and/or different directions of which the laser light is emitted.

A further object of the present invention is to provide a laser hand piece which is provided with a head attachment mechanism for releasably attaching a head to the leading end of the shank in a positive manner.

A yet further object of the present invention is to provide a laser hand piece which is provided with optical means which, when mounted on a head, facilitates the optical axis alignment and which minimizes the transmission loss of laser light.

A further object of the present invention is to provide a laser hand piece in which the direction of a contra type head attached to the leading end of the shank can be varied depending upon an affected or diseased part of a body.

A further object of the present invention is to provide a laser hand piece which, when used for cutting or drilling an affected or diseased part, can maintain the affected or diseased part being operated or treated clean.

A laser hand piece in accordance with the present invention comprises a shank upon which is mounted the light emitting end of a laser light transmission means, a head which is provided with a converging means and/or reflecting means and which is adapted to be releasably attached to the leading end of the shank and a head attachment means which is attached to the leading end of the shank for releasably attaching the head to the shank. A suitable head can be selected from the group consisting of heads which have different focal length and/or different directions in which the laser light is emitted. The head attachment means comprises a slider which is movably fitted into a hole which in turn is extended in the direction of the center line, an engaging member slidably fitted into a front end guide hole, an arresting member which is slidably fitted into a rear end guide hole, an attachment ring fitted around the rear end guide hole and a circumferentially extended groove formed at the inner wall surface of the rear end portion of the head. Depending upon an affected or diseased part of a body, one may select a suitable head and attach it to the shank. A curved prism or a semispherical prism in which a laser light reflecting surface is defined by flat surface and a laser light incident surface and a laser light emitting surface are defined by curved surfaces is mounted in the bent portion adjacent to the leading end of a contra type head which redirects the laser light. As a result, the optical axis alignment of optical means may be much facilitated and the transmission loss of laser light can be reduced to a minimum. In addition, the direction of a contra type head attached to the leading end of the shank can be varied arbitrarily so that the handling of the laser hand piece can be much facilitated. Furthermore, according to one aspect of the present invention, the compressed air and/or water is blown from the leading end of the head so that when the laser hand piece is used for surgical operations, an operated or treated part can be always maintained clean.

BRIEF DESCRIPTION OF THE DRAWINGS

FIG. 3 is a sectional view of a leading end portion of a shank and a head of the embodiment as shown in FIG. 2;

FIG. 4A is another sectional view of a leading end portion of a shank and a head of the embodiment as shown in FIG. 2;

Same reference numerals are used to designate similar parts through the figures.

CONCRETE DESCRIPTION OF PRIOR ART

Figure 1A:
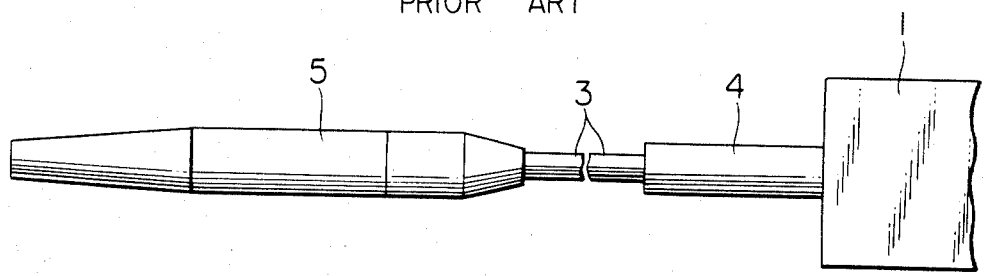
FIG. 1A shows the construction of a prior art laser device.
Figure 1B:
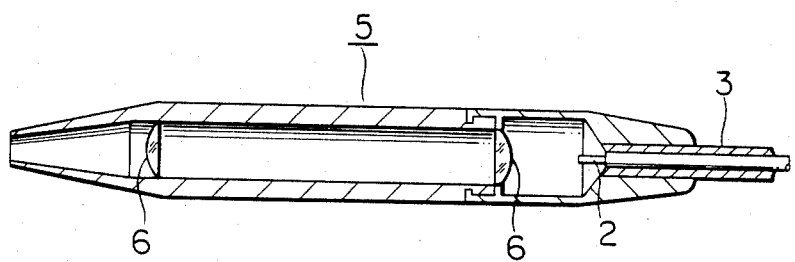
FIG. 1B is a sectional view thereof.

FIG. 1 shows a prior art laser hand piece. Reference numeral 1 denotes a laser oscillator; 2, an optical fiber for transmitting the laser light emitted from the laser oscillator 1 (See FIG. 1B); 3, a hose for covering the optical fiber 2; 4, a plug connected to the rear end of the optical fiber 2 and adapted to cause the laser light incident end of the optical fiber 2 to be positioned in opposed relationship with a laser light output end when the plug 4 is inserted into the laser oscillator 1; and 5, a hollow shank into which are mounted two converging lenses 6. The leading end of the optical fiber 2 is fixed to the rear end of the shank 5 in such a way that the laser light emitting end of the optical fiber 2 is aligned with the optical axis of the lenses 6.

In the prior art laser hand piece of the type described above, when the laser light is emitted from the laser oscillator 1, it is transmitted through the optical fiber 2 and emitted from the laser light emitting end thereof so as to be focused at a point adjacent to the leading end of the shank 5 through the lenses 6. Therefore, when the laser light is focused at an affected or diseased part of a body, the affected or diseased part can be cut off or drilled.

In order to cut off or drill an affected or diseased part of a body, a straight shank 5 with lenses 6 having a long focal length, a straight shank 5 with lenses 6 having a short focal length or a contrangle shank (not shown) in which not only converging lenses but also a total reflection prism or mirror are mounted must be selected depending upon the position of the affected or diseased part. Then, depending upon the selected shank 5, the optical fiber 2 and the plug 4 must be replaced. Thus, the prior art laser hand piece has a problem that the replacement of a laser hand piece becomes complicated. In addition, each shank 5 has its own associated optical fiber and plug, so that the cost of the laser hand piece is expensive and the cost for repair and maintenance also becomes expensive. There is a further problem that laser hand pieces used for surgical operations must be disinfected or sterilized, so that the handling of laser light hand pieces becomes complicated or troublesome.

DESCRIPTION OF THE PREFERRED EMBODIMENTS

Figure 2:
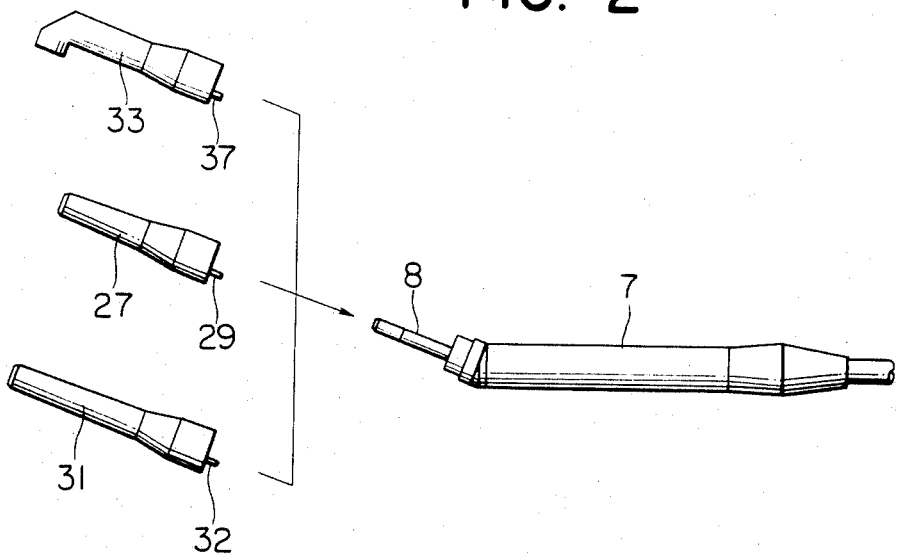
FIG. 2 shows a first embodiment of a laser hand piece in accordance with the present invention.
Figure 4B:
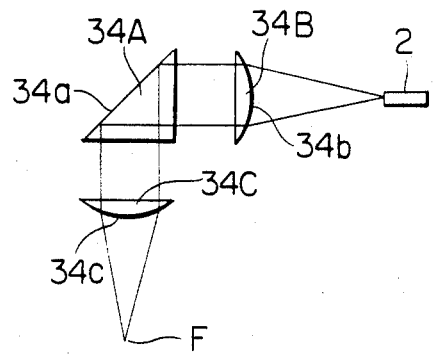
FIGS. 4B and 4C are views used to explain the underlying principle of a curved prism used in the present invention.
Figure 4C:
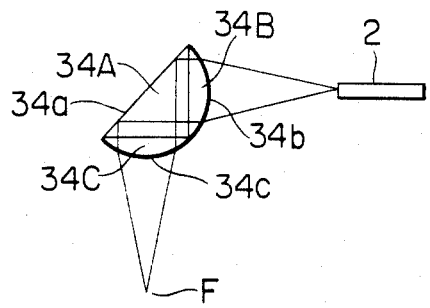

FIG. 2 shows the construction of a first embodiment of a laser hand piece in accordance with the present invention; FIG. 3 shows in detail the construction of the first embodiment; FIGS. 4A, 4B and 4C show modifications thereof; and FIGS. 5A and 5B, FIGS. 6A and 6B and FIGS. 7A and 7B show the construction and mode of operation of a head attachment device. Reference numeral 7 denotes a cylindrical contra type shank and an optical fiber holder 8 is extended outwardly from the center of an inclined leading end of the shank 7. A hose 3 is securely attached in the shank 7 adjacent to the leading end portion thereof and the light emitting end of the optical fiber 2 is securely attached to the inside of the fiber holder 8. Reference numeral 9 designates a water inlet formed at the leading end of the shank 7; 10, a water feed pipe which is fitted adjacent the hose 3, optical fiber 2, the leading end of the water feed pipe 10 being connected to the water inlet 9 while the rear end thereof being connected to a water source (not shown); 11, an O-ring fitted into the shank 7 adjacent to the water inlet 9; 12, a guide hole formed in the direction of the center line adjacent to the leading end of the shank 7; 13, a guide hole formed through the cylindrical wall of the shank 7 in the radially outward direction from the leading end portion of the guide hole 12, the outer diameter of the guide hole 13 being smaller than the inner diameter thereof; 14, a guide hole formed through the cylindrical wall of the shank 7 in the radially outward direction from the rear end portion of the guide hole 12; 15, a slider whose both ends are tapered or inclined and which is slidably fitted into the guide hole 12; 16, an engaging ball which is slidably fitted into the guide hole 13 and which is made into contact with the tapered leading end of the slider 15; 17, an arresting ball which is slidably fitted into the guide hole 14 and which is made into contact with the tapered rear end of the slider 15; 18, an attachment ring which has one release hole 19 and two click holes 20 which are formed in the inner surface wall of the attachment ring 18, the attachment ring 18 being rotatably fitted over the leading end of the shank 7 so as to cover the guide hole 14; 22, a stopper recess which is formed circumferentially in the outer wall surface of the leading end of the shank 7; 23, a screw extended through the cylindrical wall of the attachment ring 18, the leading end of the screw 23 being inserted into the stopper recess 22; 24, a hole formed at the outer wall surface of the leading end of the shank 7; 25, a ball inserted into the hole 24; 26, a bias spring adapted to bias the ball 25 in the radial direction so that the ball 25 is made into contact with the inner wall surface of the attachment ring 18; 27, a straight type head; 28, a lens which has a short focal length and which is mounted at the leading end of the head 27; 29, a pin extended from the rear end of the head 27 so as to stop water; 30, an engaging groove formed circumferentially at the inner wall surface of the rear end of the head 27; 31, a straight type head with a lens of a long focal length (not shown) being mounted at the leading end thereof and with a pin 32 extended from the rear end thereof so as to stop water, the head 31 having a circumferentially extended engaging groove (not shown) formed at the inner wall surface of the rear end thereof, the internal construction of the head 31 being substantially similar to that of the head 27; 33, an angle-shaped head with a position adjusting screw 33a disposed at the bend portion thereof; 34, a total reflection type curved prism which is mounted on the position adjusting screw 33a, the curved prism 34 having a flat surface 34a at which the laser light is reflected, a curved laser light incident surface 34b and a curved laser light emitting surface 34c, the curved prism 34 having the same function as a combination of a total reflection prism 34A with a condenser lens 34B being bonded to the laser light incident surface of the prism 34A and an objective lens 34C bonded to the laser light emitting surface of the prism 34A as shown in FIGS. 4B and 4C, the optical axis of the curved prism 34 being aligned with the optical axis of the light emitting end of the optical fiber 2 by tightening or loosening the position adjusting screw 33a; 35, a water passage extended from an injection hole 36 of the leading open end of the head 33 toward the rear end thereof; 37, a connection pipe extended from the rear end of the water passage 35; and 38, an engaging groove which is circumferentially formed at the inner wall surface of the rear end of the head 33.

Figure 5A:
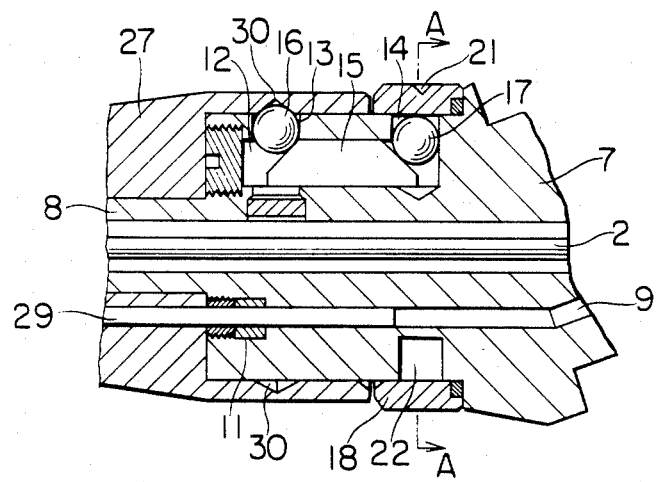
FIGS. 5A and 5B, FIGS. 6A and 6B and FIGS. 7A and 7B are views used to explain how a head is attached to or released from the leading end of the shank.
Figure 5B:
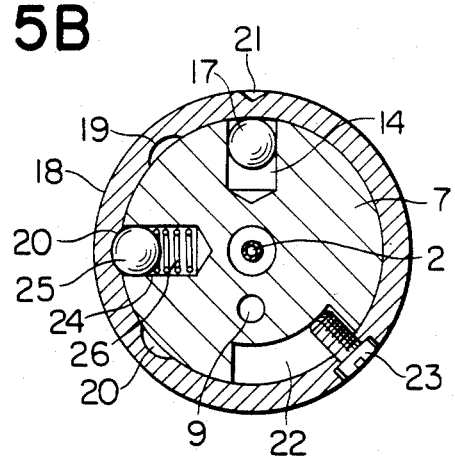
Figure 6A:
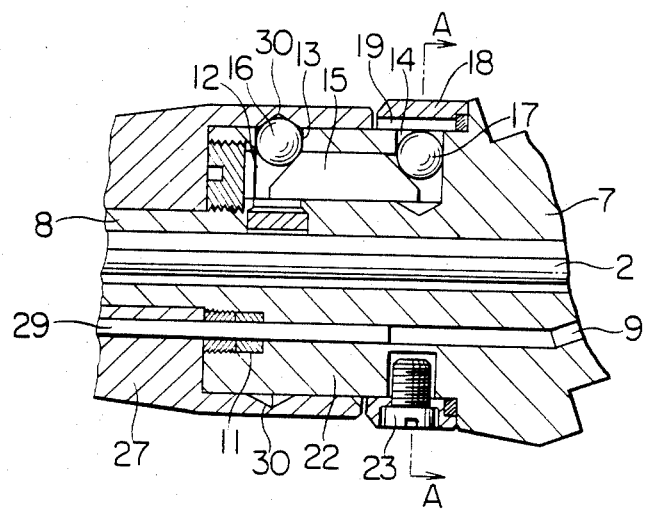
Figure 6B:
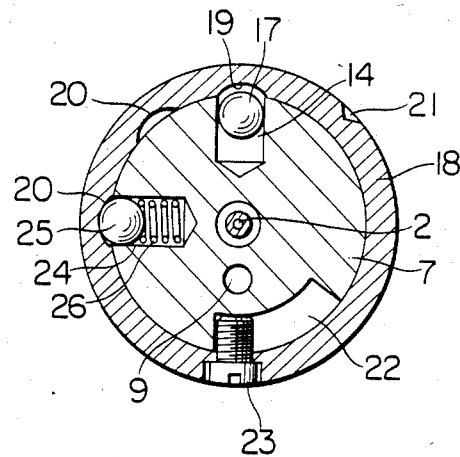
Figure 7A:
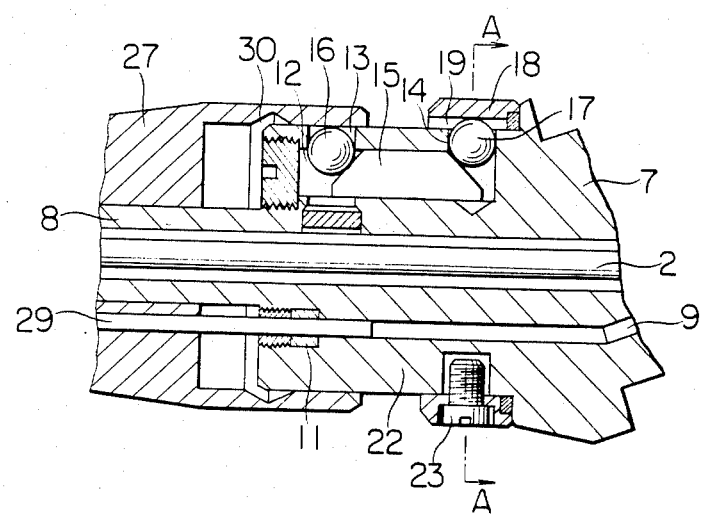
Figure 7B:
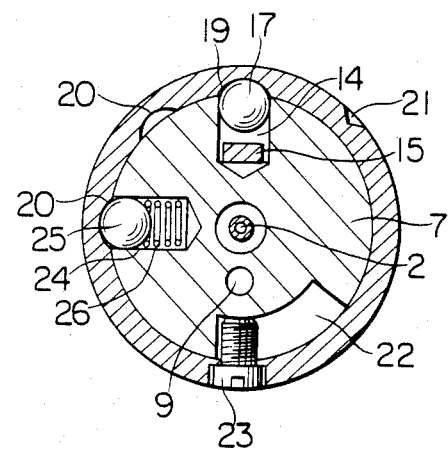

According to the first embodiment whose construction is described above, in order to remove the head 27 from the leading end of the shank 7, the attachment ring 18 is rotated in the clockwise direction in FIG. 5B until the release hole 19 is aligned with the guide hole 14 (See FIGS. 6A and 6B). Then there exists a space between the arresting ball 17 and the attachment ring 18 so that the arresting ball 17 may be moved upwardly as shown. Thereafter, the head 27 is pulled toward the left in the figure so that the engaging ball 16 which is fitted from the guide hole 13 into the engaging groove 30 is forced downwardly in the figure by the inner wall surface of the head 27. As a result, the engaging ball 16 is caused to move downwardly in the figure while the slider 15 is displaced to the right and the arresting ball 17 is moved upwardly in the figure. As a consequence, the engaging ball 16 is kept in the guide hole 13 (See FIGS. 7A and 7B), so that the head 27 can be removed from the leading end of the shank 7. In order to attach, for example, the head 27 to the leading end of the shank 7, the guide hole 14 of the attachment ring 18 is aligned with the release hole 19 (See FIGS. 7A and 7B). The pin 29 is inserted into the water inlet 9 and also the leading end of the shank 7 is inserted into the head 27. Thereafter, the attachment ring 18 is rotated in the counterclockwise direction in FIG. 7B. Then, the arresting ball 17 is forced downward by the inner wall surface of the attachment ring 18 (See FIGS. 5A and 5B), so that the arresting ball 17 is displaced downward in the figure while the slider 15 is caused to move to the left and the engaging ball 16 is caused to move upward in the figure. As a result, the engaging ball 16 engages with the engaging groove 30 and the arresting ball 17 is inserted into the guide hole 14. The engaging ball 16 is kept in the engaging groove 30, so that the head 27 is attached to the leading end of the shank 7. Thereafter, the laser light is emitted from the laser oscillator 1 and transmitted through the optical fiber 2. The laser light is emitted from the laser light emitting end of the optical fiber 2 and focused through the lens 28 at a point adjacent to the leading end of the head 27. Therefore, when the laser light is irradiated against an affected or diseased part of a body, the affected or diseased part can be cut off or drilled. Depending upon an affected or diseased part, the head 31 can be attached to the leading end of the shank 7 in a manner substantially similar to that described above with conjunction with the head 27. The laser light emitted from the laser oscillator 1 is transmitted through the optical fiber 2 and emitted from the laser light emitting end thereof. Thereafter, the laser light is focused through a lens at a point spaced apart by a relatively long distance from the lead end of the head 31. Therefore, when the laser light is irradiated against an affected or diseased part of a body, the affected or diseased part can be cut off or drilled. Depending upon an affected or diseased part, the head 33 is attached to the leading end of the shank 7. The laser light emitted from the laser oscillator 1 is transmitted through the optical fiber 2 and emitted from the laser light emitting end thereof. Then, the laser light is redirected at a right angle by the reflecting surface 34a of the curved prism 34 and is focused at a point adjacent to the leading end of the head 33 by means of the incident and emitting surfaces 34b and 34c of the curved prism 34. Therefore, when the laser light is irradiated against an affected or diseased part of a body, the affected or diseased part can be cut off or drilled.

The shank 7 may be provided with an air supply means which is similar to the water supply means consisting of the water inlet 9, the water pipe 10 and the O-ring 11 and the head 33 is also provided with an air supply means which is substantially similar in construction with the water supply means consisting of the water passage 35 and the connecting pipe 37. Therefore, the compressed air can be blown against an affected or diseased part so that a liquid accumulated at the affected or diseased part and the water which is blown through the injection hole 36 so as to clean the affected or diseased part can be removed. In this case, the operation of the affected or diseased part can be much facilitated. The curved prism 34 may be a semispherical prism whose all semispherical surface including the laser light incident and emitting surfaces is defined by one radius.

Figure 8A:
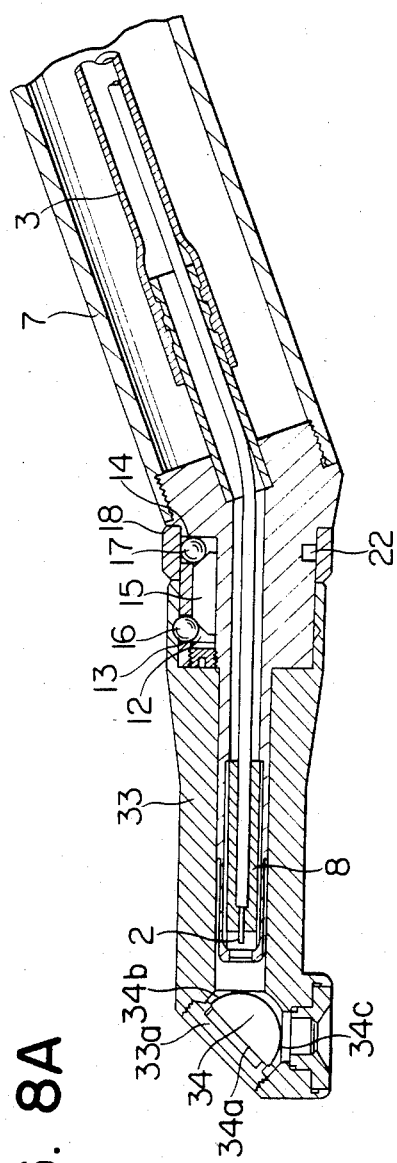
FIG. 8A is a sectional view of a leading end portion of a shank and a head of a second embodiment of a laser hand piece in accordance with the present invention.

FIG. 8A shows another embodiment of a laser hand piece in accordance with the present invention. According to the second embodiment, the water supply means comprising the water inlet 9, the water supply pipe 10 and the O-ring 11 as shown in FIG. 4A is removed and the water supply means comprising the water passage 35 and the connecting pipe 37 is removed from the head 33.

Figure 8B:
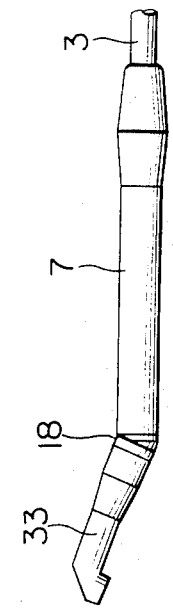
FIGS. 8B and 8C are views used to explain the mode of operation of heads in accordance with the present invention.
Figure 8C:
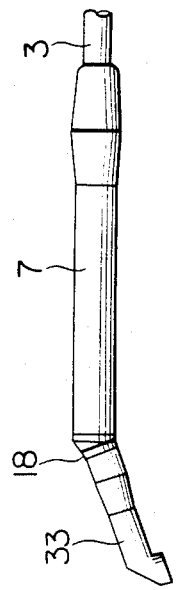

According to the second embodiment, the attachment ring 18 is rotated to the position as shown in FIGS. 6A and 6B or FIGS. 7A and 7B. Then, the engaging ball 16 is released from the engaging groove 38 so that the head 33 which is attached to the leading end of the shank 7 can be rotated about the axis of the fiber holder 8. After the direction of the head 33 is determined depending upon an affected or diseased part, the attachment ring 18 is rotated again to the position as shown in FIGS. 5A and 5B. Then, the engaging ball 16 engages with the engaging groove 38 so that the head 33 is attached to the shank 7 in such a way as shown in FIGS. 8B and 8C.

So far the laser hand piece in accordance with the present invention has been described in detail as being used in the case of a surgical operation, but it is to be understood that the laser hand piece of the present invention can be equally used in the case of machining or fabricating ornaments.

As described above, according to the present invention, a laser hand piece comprises a shank in which is mounted a laser light emitting end of a laser light transmission means, a head in which is disposed a converging means or in which are disposed a reflection means and a converging means and a head attachment means for releasably attaching the head to the leading end of the shank. A head may be selected from a group of heads provided with optical means of different focal lengths, heads provided with an optical means for redirecting the laser light and heads provided with a water supply means and an air supply means. That is, a suitable head can be selected depending upon an affected or diseased part of a body and can be attached or released by an operator so that the function of the laser hand piece can be easily varied in accordance with a need. Furthermore, the present invention provides a laser hand piece comprising one shank and a plurality of heads so that the cost of the laser hand piece can be decreased and the cost for repair and maintenance can be also lowered. In the case of a laser hand piece used for surgical operations, the laser hand piece can be easily disinfected or sterilized. In addition, when a curved prism or a semispherical prism is used in a contra type head, the optical axes of a condenser lens, a total reflection prism and an objective lens can be simultaneously aligned by making the alignment of the optical axis of the total reflection prism or semispherical prism. As a result, the construction of the contra type head can be made simple. Furthermore, the condenser lens is incorporated with the total reflection prism and also the total reflection prism is incorporated with the objective lens so that the transmission loss of the laser light can be minimized. Moreover, the optical axis alignment of the curved prism or semispherical prism can be easily carried out by means of the position adjusting screw threaded through the bent portion adjacent to the lead end of the contra type head. Since the direction of the contra type head attached to the leading end of the shank can be varied arbitrarily depending upon an affected or diseased part of a body, it becomes easy to cut off or drill an affected or diseased part. Furthermore, the air and/or water can be injected to a part cut or drilled by the laser light so that the cut or drilled part can be always maintained clean.

What is claimed is:

1. A laser hand piece for supplying laser light to a body part for cutting and drilling the same, comprising:
   a shank having a distal end;
   fiber holder means secured to said shank at the distal end thereof, said fiber holder means having a distal end;
   an optical fiber extending through said shank and said fiber holder means and terminating at the distal end of said fiber holder means, said optical fiber being adapted to receive said laser light from laser light transmission means;
   a head including laser light converging means for converging laser light from said optical fiber onto said body part; and
   head attachment means secured to the distal end of said shank for releasably attaching said head to said shank in surrounding relation to said fiber holder means, said head attachment means including an annular guide hole formed adjacent the distal end of said shank and which extends axially in line in the direction of the center line of said fiber holder means, a front end guide hole extending radially outward of the front end of said annular guide hole, a rear end guide hole which extends radially outward of the rear end of said annular guide hole, a slider slidably positioned in said annular guide hole and having leading and rear inclined ends, an engaging member slidably positioned in said front end guide hole and which engages with said inclined leading end of said slider, an arresting member slidably positioned in said rear end guide hole and which engages with said inclined rear end of said slider, an attachment ring positioned around said rear end guide hole, a hole engageable with said arresting member formed in an inner wall surface of said attachment ring, and a circumferential groove formed in an inner wall surface at the proximal end of said head in surrounding relation to said front end guide hole.

2. A laser hand piece as set forth in claim 1, wherein said head is selected from a group of heads, each head of which has at least one of a different focal length and a different direction of laser light emission, from each other head of the group.

3. A laser hand piece as set forth in claim 2, wherein at least one of the heads is of a contra type having a distal end which is bent.

4. A laser hand piece as set forth in claim 3, wherein each said contra type includes a bent portion having one of a curved prism and a semispherical prism, each prism having a flat laser light reflecting surface and curved laser light incident and emitting surfaces.

5. A laser hand piece as set forth in claim 4, wherein each said prism is secured to a position adjusting screw which in turn is screwed through said bent portion of said contra type head.

6. A laser hand piece as set forth in claim 3, wherein said head is rotatably secured to the distal end of said shank by said head attachment means, so that the direction of laser light emission from said contra type head can be varied in the circumferential direction thereof.

7. A laser hand piece as set forth in claim 1, wherein said head includes a supply duct extending to the distal end thereof through which compressed air and water can be supplied.

* * * * *